(12) United States Patent
Vrba

(10) Patent No.: US 6,254,611 B1
(45) Date of Patent: *Jul. 3, 2001

(54) STENT DEPLOYMENT CATHETER WITH MIDSHAFT SEAL

(75) Inventor: Anthony C. Vrba, Maple Grove, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/369,922

(22) Filed: Aug. 6, 1999

Related U.S. Application Data

(63) Continuation of application No. 09/071,484, filed on May 27, 1998, now Pat. No. 5,957,930, which is a continuation-in-part of application No. 08/722,834, filed on Sep. 27, 1996, now Pat. No. 5,772,669.

(51) Int. Cl.[7] ........................................... A61F 11/00
(52) U.S. Cl. ................................ 606/108; 606/195
(58) Field of Search ............................ 606/108, 195, 606/194, 198; 623/1, 12; 604/96

(56) References Cited

U.S. PATENT DOCUMENTS

| 4,580,568 | 4/1986 | Gianturco . | |
|---|---|---|---|
| 4,732,152 | 3/1988 | Wallsten et al. | 128/343 |
| 4,787,899 | 11/1988 | Lazarus . | |
| 4,848,343 | 7/1989 | Wallsten et al. . | |
| 4,998,539 | 3/1991 | Delsanti . | |
| 5,078,720 | 1/1992 | Burton et al. . | |
| 5,108,416 | 4/1992 | Ryan et al. . | |
| 5,147,379 | * 9/1992 | Sabbaghian et al. | 606/108 |
| 5,151,105 | * 9/1992 | Kwan-Gett | 623/1 |
| 5,158,548 | 10/1992 | Lau et al. . | |
| 5,180,368 | 1/1993 | Garrison . | |
| 5,188,635 | 2/1993 | Radtke . | |
| 5,192,297 | 3/1993 | Hull . | |
| 5,201,757 | * 4/1993 | Heyn et al. | 606/198 |
| 5,242,399 | 9/1993 | Lau et al. . | |
| 5,250,070 | 10/1993 | Parodi . | |
| 5,263,963 | 11/1993 | Garrison et al. . | |
| 5,290,310 | * 3/1994 | Makower et al. | 606/108 |
| 5,306,294 | 4/1994 | Winston et al. . | |
| 5,338,295 | 8/1994 | Cornelius et al. . | |
| 5,344,426 | 9/1994 | Lau et al. . | |
| 5,360,401 | 11/1994 | Turnland . | |
| 5,372,600 | 12/1994 | Beyar et al. . | |
| 5,389,100 | 2/1995 | Bacich et al. . | |
| 5,411,507 | 5/1995 | Heckele . | |
| 5,445,646 | 8/1995 | Euteneuer et al. . | |
| 5,456,667 | 10/1995 | Ham et al. . | |
| 5,458,615 | 10/1995 | Klemm et al. . | |
| 5,484,444 | 1/1996 | Braunschweiler et al. . | |
| 5,507,768 | 4/1996 | Lau et al. . | |
| 5,534,007 | * 7/1996 | St. Germain et al. | 606/108 |

(List continued on next page.)

FOREIGN PATENT DOCUMENTS

| 0 505 686 A1 | 9/1992 | (EP) . |
|---|---|---|
| 0 627 201 A1 | 12/1994 | (EP) . |
| WO 91/17789 | 11/1991 | (WO) . |
| WO 93/01849 | 2/1993 | (WO) . |

Primary Examiner—Gene Mancene
Assistant Examiner—Pedro Philogene
(74) Attorney, Agent, or Firm—Vidas, Arrett & Steinkra

(57) ABSTRACT

The present invention provides an improved stent delivery catheter. The stent delivery system comprises a catheter with a retractable sheath arranged concentrically near its distal end. The retractable sheath is connected to a pull wire for retraction. A sliding seal connects the proximal end of the retractable sheath and the catheter. This seal forms a fluid tight chamber when the retractable sheath is in the unretracted position, allowing the delivery system to be prepared by filling the fluid tight chamber with fluid to flush out air prior to insertion into the vasculature of the patient.

10 Claims, 7 Drawing Sheets

U.S. PATENT DOCUMENTS

| | | | |
|---|---|---|---|
| 5,571,168 | * 11/1996 | Toro | 623/1 |
| 5,591,172 | * 1/1997 | Bachmann et al. | 606/108 |
| 5,639,274 | 6/1997 | Fischell et al. | 604/96 |
| 5,772,669 | * 6/1998 | Vrba | 606/108 |
| 5,792,144 | * 8/1998 | Fischell et al. | 606/108 |
| 5,810,837 | 9/1998 | Hofmann et al. | 606/108 |
| 5,919,204 | 7/1999 | Lukic et al. | 606/198 |
| 5,957,930 | * 9/1999 | Vrba | 606/108 |

* cited by examiner

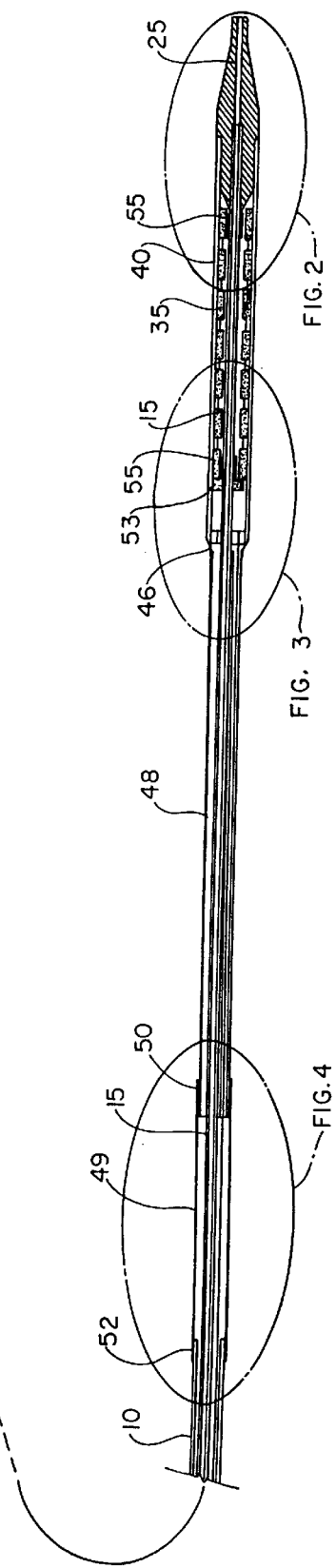

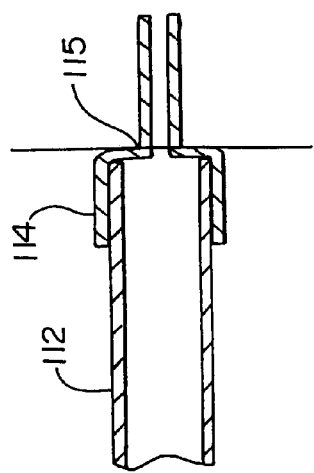
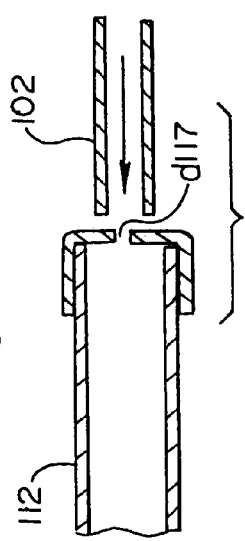
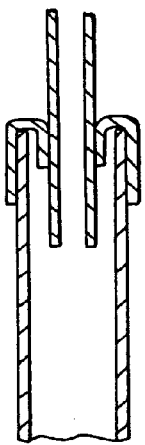

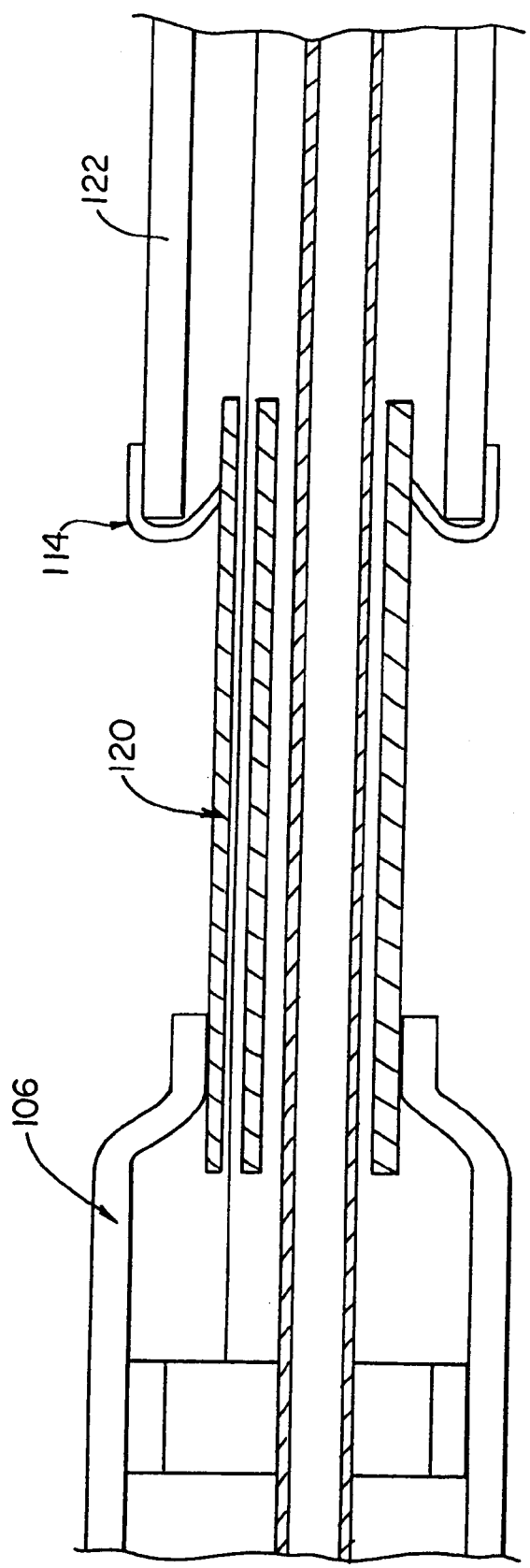

STENT DEPLOYMENT CATHETER WITH MIDSHAFT SEAL

CROSS-REFERENCE TO RELATED APPLICATIONS

This application is a continuation from U.S. patent application No. 09/071,484 filed May 27, 1998, U.S. Pat. No. 5,957,930 which was a continuation-in-part of 08/722,834 filed Sep. 27, 1996, which issued as U.S. Pat. No. 5,772,669, the entire contents of each of which are hereby incorporated by reference.

FIELD OF THE INVENTION

This invention relates to a stent delivery catheter system, such as the kind used in percutaneous transluminal coronary angioplasty (PTCA) procedures. More particularly, it relates to a stent delivery catheter employing a retractable sheath which slidingly seals with the catheter.

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon may be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a self-expanding stent or a balloon expandable stent. For the latter type, the stent is often delivered on a balloon and the balloon is used to expand the stent. The self-expanding stents may be made of shape memory materials such as nitinol or constructed of regular metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is retracted in a proximal direction on the catheter to expose the stent. After the sheath is removed, the stent is free to self-expand or be expanded with a balloon.

In a stent deployment system which utilizes a retractable sheath one problem which is encountered is the interaction of the sheath and guide catheter upon retraction. The traditional way of dealing with this is to make the retractable sheath long enough so that it will be contained in the guide catheter at all times. This increases system profile, reduces flexibility and creates excess friction upon sheath retraction.

Another problem encountered when using a retractable sheath relates to catheter preparation. This involves flushing the system with fluid to ensure no air remains in the delivery device and maintaining the fluid filled state to prevent air from entering the system before inserting it into the vasculature of the patient.

SUMMARY OF THE INVENTION

The present invention provides an improved stent delivery system. The stent delivery system comprises in a preferred embodiment, a catheter having a proximal outer shaft and a stent receiving portion adapted to receive a stent near the distal end of the catheter, a retractable distal sheath concentrically arranged around the stent receiving portion and a pull back means operatively connected to the distal sheath. The catheter is further arranged so that the retractable sheath or a member connected thereto is pulled into the proximal outer shaft of the catheter during retraction of the distal sheath thereby freeing the loaded stent. The inclusion of the retractable sheath maintains a reduced system profile and provides good flexibility.

In the preferred embodiment of the invention the basic components of the stent delivery system consist of a stent sheath, i.e., a cover means surrounding the stent at least in part but preferably fully, a pull wire arrangement or other pull back means, such as a hydraulic or screw arrangement or other means, a manifold with a slide mechanism, a catheter having a non-compressible inner shaft, an outer shaft, and two radiopaque marker bands. The stent is introduced to the body housed in a polymer sheath. The sheath is operatively connected to the manifold by a stainless steel pull wire or the like. The manifold contains a slide mechanism. Deployment is achieved by actuating the slide mechanism to retract the stent sheath thereby releasing the stent from the sheath. A non-compressible inner shaft creates a lumen for guide wire passage and fluid delivery. A multi-component outer shaft receives the sliding sheath interiorly while maintaining a fluid path between the manifold and sheath. Two radiopaque marker bands rest underneath the stent. The marker bands are spaced to match the length of the stent providing a visual guide for accurate placement and deployment.

The multi-component outer shaft preferably consists of a Polyimide stainless steel composite tube, a high density polyethylene (HDPE) proximal slide sheath, a distal HDPE dual lumen tube, and a HDPE stent sheath. The proximal slide sheath is bonded to the distal end of the composite outer tube. The stent sheath is bonded to the distal end of the dual lumen tube to form a retractable sheath means. The proximal slide sheath is sized in correspondence with the distal dual lumen tube to form a seal with the dual lumen tube. The proximal end of the dual lumen tube slides into the distal end of the proximal slide sheath to absorb the length of the stent means which is retracted when the stent sheath is moved to release the stent. Together, the dual lumen tube and the stent sheath form a retractable sheath means which is received interiorly of the outer body portion of the catheter, such as the outer shaft. This contrasts with other methods where a distal segment slides over the proximal segment or collapses to absorb a length of a retracting member.

The proximal slide sheath is stationary and is in effect an extension of the outer shaft. The distal dual lumen slides into the proximal slide sheath. The ledge formed by the outside diameter growth between the two shafts remains stationary in the anatomy once tracked to the lesion. Therefore, the ledge will not engage the anatomy during deployment. In the prior art, anatomy engagement with a sheath sliding over the proximal shaft is a distinct possibility, especially on a bend.

The distal segment's profile will be smaller with an "into" length change according to this invention compared to an "over" length change. A "collapsing" design requires a profile growth during deployment and can present a non-uniform profile when pulling the shaft back into the guide catheter.

The length of the absorbing member is minimized with an "into" or "over" design versus a "collapsing" design. Since a collapsing tube requires space even in it's collapsed position, the ratio between the required shaft length change and the absorbing member will never be one to one. The collapsing shaft's longer absorption member exposes the pull wire to buckle over a longer length. The axial length change in the pull wire caused by buckling could cause unintended stent deployment.

The inventive delivery system solves the problem of catheter preparation, maintaining the prepared condition of the system, and preventing fluid from leaking out by providing a sliding seal which forms a seal between the proximal end of the retractable sheath and the catheter body. The sliding seal maintains the prepared state and allows elimination of full length sheaths such as Imbert U.S. Pat. No. 4,875,480 without using the collapsible sheath technique of U.S. Pat. No. 5,534,007.

Other objects, features, embodiments and characteristics of the present invention, as well as the methods of operation and functions for the related elements of the structure, and the combination of parts and economics of manufacture, will become more apparent upon consideration of the following description with reference to the accompanying drawings, all of which form a part of this specification.

BRIEF DESCRIPTION OF THE FIGURES

FIG. 1 shows a side view of a stent delivery system according to the invention having a loaded stent including a cross-sectional view of the distal portion thereof and a side view of the proximal end of a stent delivery system according to the invention showing the manifold portion thereof.

FIG. 11 shows the first step in the process of making the sliding seal.

FIG. 12 shows the second step in the process of making the sliding seal.

FIG. 13 shows the final step in the process of making the sliding seal.

FIG. 14 shows a side view of a second embodiment of a sliding seal.

DETAILED DESCRIPTION OF THE INVENTION

Figure 5:
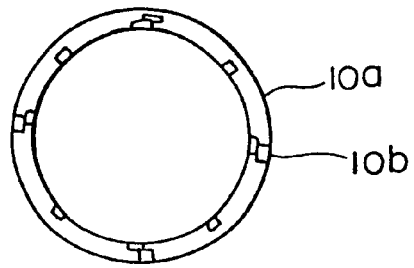
FIG. 5 is a cross-section view of the catheter outer shaft.
Figure 6:
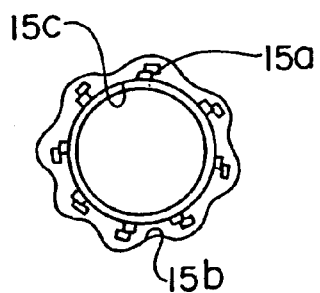
FIG. 6 is a cross-section view of the catheter inner shaft.

FIG. 1 shows a longitudinal cross-section of a specific preferred embodiment of a stent delivery system that is the subject of the present invention. The device generally comprises a catheter comprising a proximal outer shaft 10 of a predetermined length and an inner shaft (guide wire lumen) 15, the outer shaft forming an outer body portion which covers the majority of the inner shaft excluding a portion of the distal end of the inner shaft. This outer shaft 10 is characterized by a flexible tube which contains room for a pull wire and a guide wire lumen. Preferably the outer shaft 10 is comprised of a Polyimide and stainless steel ribbon composite material. The detailed structure is shown in FIG. 5 to be a tube formed of Polyimide 10*a* formed around a braided ribbon 10*b* as is known in the art. Affixed to the distal end of shaft 10 is proximal slide sheath 49 which serves as an extension of outer shaft 10 and to receive the retractable sheath means. The proximal outer shaft 10 and proximal slide sheath 49 encloses a guide wire lumen 15 which is longer than outer shaft 10 and extends through and beyond outer shaft 10 to terminate at the distal tip 25 of the catheter. Preferably the guide wire lumen 15 encloses a guide wire (not shown) which aids in the navigation of the catheter through the appropriate vessel. The guide wire lumen 15 is preferably made of flexible, but incompressible construction such as a polymer encapsulated braid or coil as shown in FIG. 6. Such construction is known in the art. The flexibility of the braid/coil construction allows the catheter to navigate through body lumens and the incompressibility of the braid/coil aids in maintaining the integrity for the catheter and aids in deployment accuracy when the sheath is being retracted during stent release. The braid/coil may be comprised of stainless steel 15*a*, encased in a polymer such as Polyimide 15*b*, with an inner layer of Teflon 15*c*.

Situated just proximal to the distal tip 25 which may be a body of urethane, is the portion of the catheter around which the stent 35 is concentrically carried. Distal tip 25 may be affixed to the catheter by an adhesive such as H.B. Fuller 3507, a urethane adhesive, or the like. The stent 35 surrounds and is carried by the guide wire lumen 15. The stent 35 is preferably a nitinol alloy or mesh self-expanding stent, but may also be a balloon expandable stent carried by an expansion balloon. Self-expanding and balloon expandable stents are well known in the art and require no further description.

Figure 3:
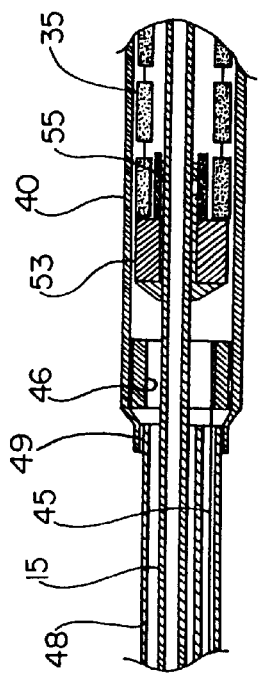
FIG. 3 is a detail view of a portion of the stent delivery system of FIG. 1 according to the invention having a loaded stent including a cross-sectional view of the retracting arrangement for the retractable sheath.
Figure 2:
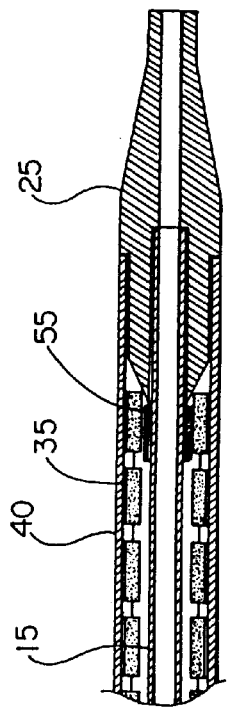
FIG. 2 is a detail view of a portion of the stent delivery system of FIG. 1 according to the invention having a loaded stent.
Figure 4:
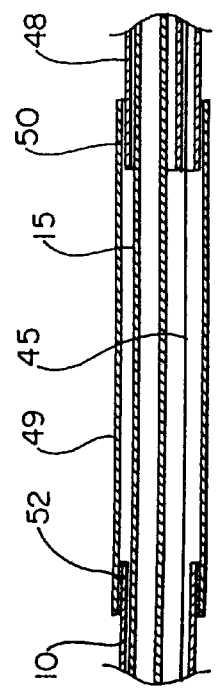
FIG. 4 is a detail view of a portion of the stent delivery system of FIG. 1 showing the arrangement for retracting the sheath into the stent delivery system.
Figure 9:
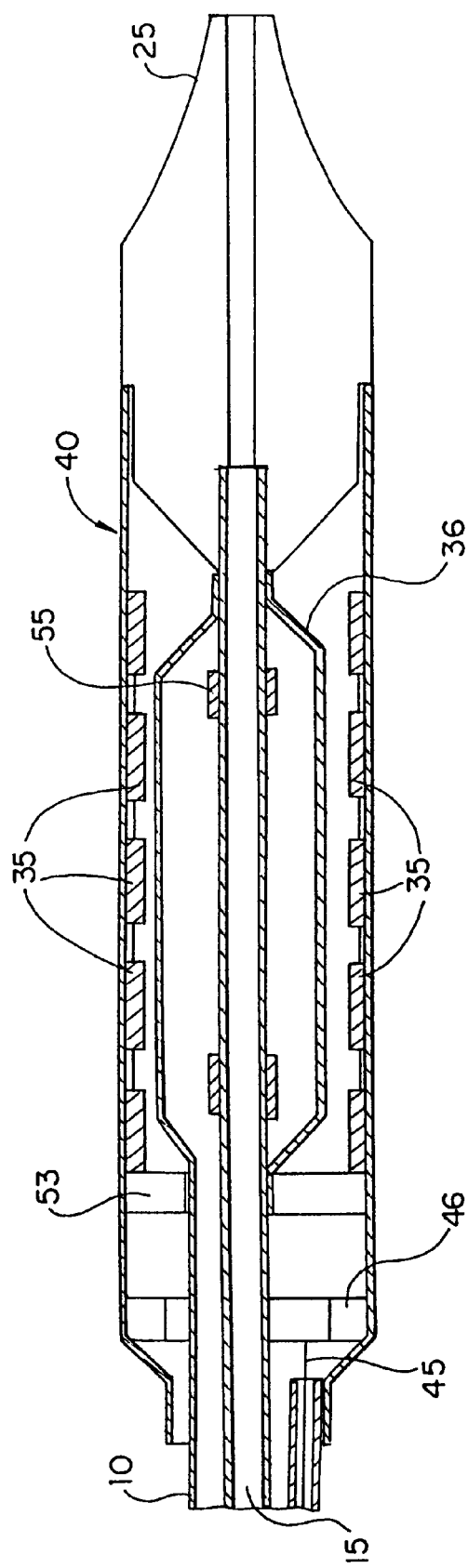
FIG. 9 shows a side view of a balloon catheter according to the invention.

The present invention further comprises a retractable distal sheath 40 which covers and contains the loaded stent 35. The retractable distal sheath 40 will hold a self-expanding stent in its reduced delivery configuration. Alternatively, the retractable distal sheath may merely contain a balloon expandable stent which is positioned over an expansion balloon 36 as shown in FIG. 9, in which the same members are used to identify elements similar to those in FIGS. 1–3. The distal sheath 40 is connected to a retracting member 45 such as a pull wire, best seen in FIG. 3, by means of a pull collar 46 which is a ring-shaped member of stainless steel affixed to the interior of sheath 40 by an appropriate adhesive such as Loctite 4011, a cyanoacrylate. As best seen in FIG. 3, collar 46 is slidably carried on guide wire lumen 15, which allows a physician to retract the distal sheath 40 from the proximal end of the catheter thus releasing the stent 35 in the targeted area of the vessel. The retractable sheath 40 may be flexible or rigid, and is generally used to retain the stent 35 and protect the vessel wall. The retractable sheath is preferably formed of a material which provides tensile strength, but is flexible, such as polyethylene.

Figure 8:
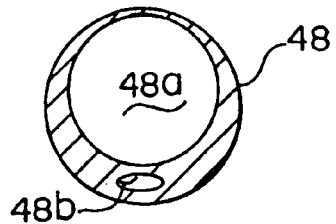
FIG. 8 is a cross-section view of the stent delivery system distal dual lumen.

The proximal end of retractable sheath 40 is affixed to a dual lumen tubular member 48 by an appropriate adhesive such as H.B. Fuller 3507. Dual lumen member 48 is also shown in FIG. 8 with large lumen 48a and smaller lumen 48b through which guide wire lumen 15 and pull wire 45 extend respectively.

Figure 7:
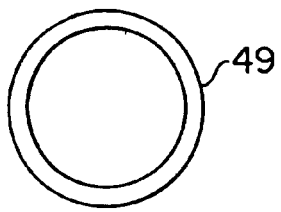
FIG. 7 is a cross-section view of the stent delivery system proximal slide sheath.

The proximal end of member 48 is received within proximal slide sheath 49 at 50 in a sliding seal to allow retraction of member 48 into slide sheath 49 when the pull wire 45 retracts sheath 40, sheath 40 and dual lumen 48 comprising a retractable sheath means which is withdrawn into the catheter body. Utilizing a slide sheath 49 of polyethylene tubing having an inside diameter of 0.049 inches and a dual lumen tube 48 of HDPE having an outside diameter of 0.047 inches is an example of an arrangement which provides a tolerance fit. Proximal slide sheath 49 is a simple cylinder in form as shown in FIG. 7. The proximal end of slide member 49 is affixed by adhesive such as H.B. Fuller 3507 to outer shaft 10 at 52 and is a continuation of shaft 10 in effect to provide a two-piece or composite outer shaft.

A bumper member 53 is also carried on guide wire lumen 15 and is positioned at the proximal end of stent 35 as shown. Bumper 53 may be of polyethylene and is affixed to guide wire lumen 15 by adhesive such as H.B. Fuller 3507 so as to prevent movement of stent 35 in a proximal direction when sheath 40 is retracted.

Marker bands 55 are included to aid in positioning and maybe affixed to inner shaft 15 by adhesive such as Loctite 4011.

At the proximal end of the catheter is a manifold structure 60 with slide mechanism 62 as is known in the art. Slide mechanism 62 is connected to pull wire 45 in known manner for retracting the sheath 40 by moving the slide proximally.

To prepare the stent delivery system the stent 35 is compressed and loaded into the stent receiving portion and covered by protective distal sheath 40. The distal sheath 40 remains covering the underlying stent 35 during the placement of the stent 35 by the delivery catheter through the patient's vasculature. During the placement of the stent 35, protective distal sheath 40 protects the patient's vasculature from the stent 35.

When in place, as the sliding member 46 is pulled back, the distal sheath 40 begins to retract. The stent is prevented from moving proximally with the sheath by the bumper 53 and therefore, the stent 35 begins to release and expand while the sheath begins to expose it. After the stent 35 is expanded and in place, the catheter is withdrawn. It should be understood that a balloon expandable stent could also be utilized by arranging the stent around an optional placement balloon (36 as shown in FIG. 9). Once the sheath 40 is fully retracted the placement balloon would be inflated through its inflation lumen to deploy the stent.

Preferably stent 35 is self expanding, such as a nitinol alloy stent, or it may be expanded by means of an internal balloon positioned under the stent 35 on the distal end of the inner core 40. Those skilled in the art will recognize other suitable materials and constructions which may be employed to serve substantially the same function.

It should be understood that other mechanical methods of retracting the pull back wire, besides the manifold apparatus disclosed herein, may be employed.

The present invention may be incorporated into both of the two basic types of catheters used in combination with a guide wire, commonly referred to as over-the-wire (OTW) catheters and rapid-exchange (RX) catheters. The construction and use of both over-the-wire and rapid-exchange catheters are well known in the art. The usable length of the delivery catheter is approximately 135 cm. For a rapid-exchange catheter the distance from where the guide wire accesses the guide wire lumen to the distal tip will be approximately 5 cm to 35 cm.

Figure 10:
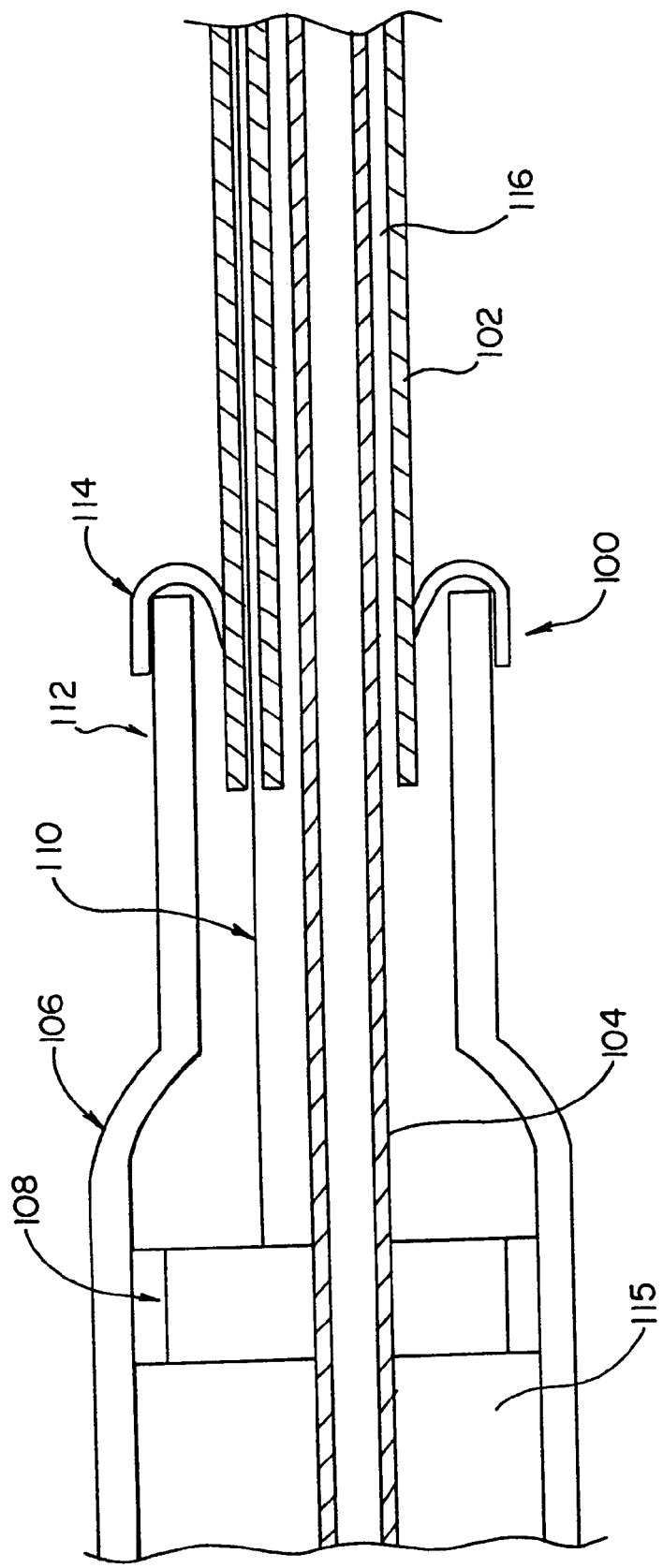
FIG. 10 shows a side view of a first embodiment of a sliding seal.

Referring now to FIG. 10, the distal end of a stent delivery system 100 is shown with an outer shaft 102 and an inner shaft 104. Retractable sheath 106 is operatively connected for retraction to pull collar 108, which is connected to pull wire 110, which extends to the proximal end of the delivery system. The proximal end 112 of retractable sheath 106 is slidingly sealed to outer shaft 102 by sliding seal 114. In the preferred embodiment sliding seal 114 is made of a polyolefin ionomer copolymer, such as a Suryln® polymer, but could also be molded out of an elastic polymer.

Referring now to FIGS. 11–14, sliding seal 114 is manufactured by heat shrinking 114 over proximal end 112, trimming 114 at the transition point 115 from the narrow diameter of the seal 114 to the wider diameter of the seal portion 114 around 112. Then 102 is pushed in to invaginate and form seal 114. The diameter d, shown at 117 in FIG. 12 is smaller than the diameter of of 102, causing the sliding seal to push downward forming the seal against 102. The fluid pressure in the gap between 112 and 102 also pushes downward on seal 114 to help seal 114 maintain its fluid-tight seal.

As an alternatively to the manufacturing process of FIGS. 12–14, the same part could be molded with the desired shape, slide on proximal end 112 and adhesively bonded.

When in the unretracted position, sliding seal 114, retractable sheath 106 and the distal tip 25 (see FIG. 1) form a fluid tight chamber 115. Inflation lumen 116 is used to fill the fluid tight chamber 115 to flush the chamber of air prior to insertion of the stent delivery system into the vasculature of the patient. The inventive sliding seal 114 provides an advantage over full length sheath devices, such as that disclosed in Imbert U.S. Pat. No. 4,875,480, by eliminating the full length sheath, while maintaining the catheter preparation without the need for the collapsible sheath of U.S. Pat. No. 5,534,007, the entire contents of which are hereby incorporated by reference. The inventive sliding seal 114 allows for a smaller system profile then a collapsible sheath system in the deployed state and eliminates the need for a full length sheath while maintaining the prepared state.

FIG. 14 shows a delivery system much like the system described in FIGS. 1–9 in which the retractable sheath 106 is adhesively bonded to catheter section 120, which is retracted into outer shaft 122 by pull wire 110 and annular collar 108. Sliding seal 114 is adhesively bonded to outer shaft 122 and slidingly seals outer shaft 122 to catheter section 120. This embodiment provides an advantage over full length sheath devices, such as that disclosed in Imbert U.S. Pat. No. 4,875,480, by eliminating the full length sheath, while maintaining the catheter preparation without the need for the collapsible sheath of U.S. Pat. No. 5,534,007.

It should be understood that the pull wire may extend to the proximal end of the catheter or may be actuated hydraulically closer to the distal end of the device, as disclosed in commonly owned U.S. Pat. No. 5,571,135 or U.S. 5,445,646, the entire contents of which are hereby incorporated by reference. The pull wire may also take the form of the nitinol retraction wire disclosed in commonly owned U.S. patent applications Ser. No's 08/941978 and 08/947619, the entire contents of which are hereby incorporated by reference.

The above disclosure is intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A stent delivery system comprising:

an elongate flexible catheter comprised of an outer tube and an inner tube, the inner tube being carried within the outer tube and a portion of the inner tube extending beyond the distal end of the outer tube;

a distal tube having proximal and distal ends and being received over the portion of the inner tube extending beyond the distal end of the outer tube, the proximal end of the distal tube being slidably received into the distal end of the outer tube, and a sliding seal connected to the distal end of the outer tube and forming a sliding seal between the outer tube and the distal tube.

2. The stent delivery system of claim 1 further comprising a stent disposed about the inner tube.

3. The stent delivery system of claim 2 wherein the stent is balloon expandable.

4. The stent delivery system of claim 2 wherein the stent is self-expanding.

5. The stent delivery system of claim 1 in an over-the-wire configuration.

6. A delivery system comprising:

a catheter having proximal and distal ends;

a retractable sheath having proximal and distal ends arranged around the catheter near its distal end, the retractable sheath being connected to a pull wire for retraction, the pull wire extending to the proximal end of the catheter, and a sliding seal connected to the proximal end of the retractable sheath and forming a sliding seal between the retractable sheath and the catheter.

7. The delivery system of claim 6 further comprising a stent disposed about the catheter.

8. The delivery system of claim 7 wherein the stent is balloon expandable.

9. The delivery system of claim 7 wherein the stent is self-expanding.

10. The stent delivery system of claim 6 in an over-the-wire configuration.

* * * * *